US008021302B2

(12) United States Patent
Sato

(10) Patent No.: US 8,021,302 B2
(45) Date of Patent: Sep. 20, 2011

(54) ULTRASONIC APPARATUS AND ULTRASONIC DIAGNOSTIC METHOD

(75) Inventor: Takeshi Sato, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 628 days.

(21) Appl. No.: 12/043,681

(22) Filed: Mar. 6, 2008

(65) Prior Publication Data

US 2008/0221449 A1    Sep. 11, 2008

(30) Foreign Application Priority Data

Mar. 7, 2007    (JP) .................. 2007-057314

(51) Int. Cl.
*A61B 8/14*    (2006.01)

(52) U.S. Cl. ...................... 600/442; 600/437
(58) Field of Classification Search .......... 600/447, 600/455, 458, 443, 442; 369/59.18, 124.15
See application file for complete search history.

(56) References Cited

U.S. PATENT DOCUMENTS

| | | | |
|---|---|---|---|
| 4,295,221 A * | 10/1981 | Henoch et al. ............ 375/239 |
| 4,553,221 A * | 11/1985 | Hyatt ....................... 708/308 |
| 5,035,144 A * | 7/1991 | Aussel ....................... 73/602 |
| 5,271,404 A * | 12/1993 | Corl et al. ................. 600/454 |
| 6,213,947 B1 | 4/2001 | Phillips |
| 6,241,674 B1 | 6/2001 | Phillips et al. |
| 6,245,016 B1 * | 6/2001 | Daft et al. ................ 600/443 |
| 6,248,071 B1 * | 6/2001 | Lin ......................... 600/443 |
| 6,918,875 B2 * | 7/2005 | Moriya et al. ............ 600/443 |
| 2006/0226897 A1 * | 10/2006 | De Ruijter ................ 329/315 |

FOREIGN PATENT DOCUMENTS

| | | |
|---|---|---|
| EP | 1 346 691 A1 | 9/2003 |
| EP | 1 739 455 A1 | 1/2007 |
| JP | 3-60493 | 9/1991 |
| JP | 5-41259 | 6/1993 |
| JP | 2003-235844 | 8/2003 |
| JP | 2005-58533 | 3/2005 |

OTHER PUBLICATIONS

Marko Liebler, et al., "Full wave modeling of therapeutic ultrsound: Efficient time-domain implementation of the frequency power-law attenuation", Journal of the Acoustical Society of America, vol. 116, No. 5, XP012072599, ISSN:0001-4966, Nov. 1, 2004, pp. 2742-2750.

R. P. B. Da Costa-Félix, et al., "Broadband Ultrasonic Attenuation Measurements Using Coded Sweep Excitations", 2004 IEEE Ultrasonics Symposium, vol. 2, XP010784141, ISBN: 978-0-7803-8412-5, Aug. 23, 2004, pp. 1066-1069.

* cited by examiner

*Primary Examiner* — Unsu Jung
*Assistant Examiner* — Lawrence Laryea
(74) *Attorney, Agent, or Firm* — Oblon, Spivak, McClelland, Maier & Neustadt, L.L.P.

(57) ABSTRACT

An ultrasonic apparatus has a pulse transmission and reception unit, an envelope curve detection unit, a time difference detection unit, and an attenuation characteristic obtaining unit. The pulse transmission and reception unit transmits a first transmitted pulse that a frequency increases with time and a second transmitted pulse that the frequency decreases with time, further receives a first received pulse corresponding to the first transmitted pulse and a second received pulse corresponding to the second transmitted pulse. The envelope curve detection unit detects a first envelope curve based on the first received signal and a second envelope curve based on the second received signal, respectively. The time difference detection unit detects a time difference between the first envelope curve and the second envelope curve. The attenuation characteristic obtaining unit obtains a frequency dependent-attenuation characteristic of an ultrasonic base on the time difference.

15 Claims, 5 Drawing Sheets

ULTRASONIC APPARATUS AND ULTRASONIC DIAGNOSTIC METHOD

BACKGROUND OF THE INVENTION

1. Field of the Invention

The present invention relates to an ultrasonic apparatus and an ultrasonic diagnostic method for obtaining biological information inside an object through a transmission and a reception of an ultrasonic wave to and from the object, particularly to the ultrasonic apparatus and the ultrasonic diagnostic method capable of measuring or using a frequency dependent-attenuation affecting a ultrasonic wave in a living body.

2. Description of the Related Art

An ultrasonic apparatus is a diagnostic imaging apparatus which transmits and receives the ultrasonic wave to and from the object, such as the living body, to non-invasively obtain a tomographic image of a tissue present in the object. It is known that, when the ultrasonic apparatus transmits the ultrasonic wave in the form of plane wave to the object, the ultrasonic wave is affected by a frequency dependent attenuation (FDA) along with a propagation of the ultrasonic wave. The amount of the FDA is determined depending on the frequency dependent-attenuation coefficient $\beta$. For example, when an ultrasonic pulse having a center frequency $f_0$ of 2.5 [MHz] is transmitted to the object with a frequency dependent-attenuation coefficient $\beta=1$ [dB/MHz/cm] to obtain an ultrasonic reflection echo of a matter located at a depth of $z=10$ [cm] in the object, the ultrasonic pulse is affected by attenuation "At" expressed by a following equation (1).

$$At=2\beta \cdot f_0 \cdot z=1[dB/MHz/cm] \times 2.5[MHz] \times 10[cm] \times 2[a\ round\text{-}trip]=50\ dB \quad (1)$$

To measure the frequency dependent-attenuation coefficient $\beta$ of the living tissue by using a frequency analysis such as a fast Fourier transformation (FFT), at least a predetermined number of data sets in a target area are required. However, the value of the frequency dependent-attenuation coefficient $\beta$ is not necessarily the same even within the same object, and varies depending on an organ and pathology. Thus, it is difficult to secure a sufficient number of data sets, and the value of the frequency dependent-attenuation coefficient $\beta$ in the object is unknown. A public known ultrasonic diagnostic apparatus uses a broadband pulse wave as the ultrasonic pulse to be transmitted. Therefore, the deeper source of the ultrasonic reflection echo is located, the more the ultrasonic pulse is affected by the FDA and reduced in the center frequency.

On the other hand, to obtain a received signal received as the ultrasonic reflection echo with a good S/N (signal to noise ratio), it is important to adjust a mixing frequency used in a quadrature phase detection to the center frequency of the received signal in accordance with the depth. However, the value of the frequency dependent-attenuation coefficient $\beta$ of the object constituting the living body is unknown. Usually, therefore, a site for imaging is assumed, and the mixing frequency is changed in accordance with the depth and in consideration of an average frequency dependent-attenuation coefficient $\beta$ of the site. For example, a method of determining the value of the mixing frequency through the frequency analysis of the received signal has been proposed (e.g., Japanese Patent Application Publication (Laid-open: KOKAI) No. 2003-235844).

In the imaging in a color Doppler mode for displaying information of a blood flow speed according to an ultrasonic Doppler method, the speed "v" of the blood flow is calculated from a following equation (2) using a normalized frequency "fd" of a detected ultrasonic Doppler signal, the center frequency "fm" of the received signal, a speed of sonic "C", and a pulse repetition frequency "PRF". The normalized frequency "fd" ranges from −0.5 to 0.5.

$$v = \frac{C \cdot PRF}{2f_m} f_d \quad (2)$$

To measure the distortion of the tissue by using a tissue Doppler method, more accurate information of the blood flow speed is required. Thus, it is desired to measure and correct the center frequency of the received signal. In view of this, a method of measuring and correcting the center frequency of the received signal through the frequency analysis of the received signal has been proposed (e.g., Japanese Patent Application Publication (Laid-open: KOKAI) No. 2005-58533).

On the other hand, a technique of visualizing the frequency dependent-attenuation coefficient $\beta$ such that the frequency dependent-attenuation coefficient $\beta$ directly contributes to the diagnosis has been proposed (e.g., Japanese Examined Patent Application Publication No. 3-60493). Specifically, there is a method of calculating the frequency dependent-attenuation coefficient $\beta$ through the frequency analysis of the received signal and visualizing the calculated frequency dependent-attenuation coefficient $\beta$. Further, a method of measuring in real time the frequency dependent-attenuation coefficient $\beta$ by using a spectral moment method has been proposed (e.g., Japanese Examined Patent Application Publication (Laid-open: KOKOKU) No. 5-41259).

That is, the frequency dependent-attenuation coefficient $\beta$ of the tissue has been conventionally measured by using the frequency analysis. The method of the frequency analysis includes a method of analysis based on a frequency axis, such as a Fourier transformation, and a method of analysis based on a time axis, such as the spectral moment method.

However, the sites in the living body rarely have a uniform impedance difference. Therefore, even if the frequency analysis is performed in a certain range to measure the frequency dependent-attenuation coefficient $\beta$, the range includes a scatterer having a small impedance difference, such as a parenchyma of the liver, and a reflector having a large impedance difference, such as a blood vessel wall and a tissue boundary. Further, a ratio of the scatterer having the small impedance difference or the reflector having the large impedance difference is different from site to site in the living body.

Accordingly, if a frequency characteristic is compared between sites of different conditions, an accurate frequency dependent-attenuation coefficient $\beta$ cannot be measured. Particularly, an error is large in the intensity of the ultrasonic reflection echo required for the calculation of attenuation.

In addition, there is a circumstance in which a processing of the frequency analysis is generally complicated.

Further, an imaging according to a contrast echo method using an intravenous ultrasonic contrast agent has been recently performed. It is desired in the contrast echo method to diagnose the hemodynamics on the basis of the comparison of a degree of the contrast produced by the contrast agent among the imaged sites. As described above, however, the frequency dependent-attenuation coefficient $\beta$ varies depending on the depth and the organ. Thus, a circumstance arises in which simple comparison of a luminance of the contrasted ultrasonic image cannot be performed among the imaged sites. Therefore, it is desired to provide ultrasonic image information enabling the simple comparison of the luminance, for example, irrespective of the differences in the frequency dependent-attenuation coefficient β, and thus more useful for the diagnosis.

SUMMARY OF THE INVENTION

The present invention has taken into consideration the above-described problems, and it is an object of the present invention to provide an ultrasonic apparatus and an ultrasonic diagnostic method which is able to measure a frequency dependent-attenuation that an ultrasonic is affected with a living body, through an easy-to-use processing.

Further, the present invention has taken into consideration the above-described problems, and it is an object of the present invention to provide the ultrasonic apparatus and the ultrasonic diagnostic method which is able to supply utilitarian diagnostic information by using a measured value of the frequency dependent-attenuation that the ultrasonic is affected with the living body.

To solve the above-described problems, the present invention provides the ultrasonic apparatus, comprising: a pulse transmission and reception unit configured to transmit a first transmitted pulse that a frequency increases with time and a second transmitted pulse that the frequency decreases with time, further receive a first received pulse corresponding to the first transmitted pulse and a second received pulse corresponding to the second transmitted pulse; an envelope curve detection unit configured to detect a first envelope curve based on the first received signal and a second envelope curve based on the second received signal, respectively; a time difference detection unit configured to detect a time difference between the first envelope curve and the second envelope curve; and an attenuation characteristic obtaining unit configured to obtain a frequency dependent-attenuation characteristic of an ultrasonic base on the time difference.

To solve the above-described problems, the present invention provides an ultrasonic diagnostic method, comprising: a pulse generation step of generating a pulse for applying a first transmitted pulse that a frequency increases with time and a second transmitted pulse that the frequency decreases with time to a probe; an envelope curve detection step of detecting a first envelope curve based on the first received signal and a second envelope curve based on the second received signal, respectively; a time difference detection step of detecting a time difference between the first envelope curve and the second envelope curve; and an attenuation characteristic obtaining step of obtaining a frequency dependent-attenuation characteristic of an ultrasonic based on the time difference.

DESCRIPTION OF THE PREFERRED EMBODIMENTS

With reference to the accompanying drawings, description will now be made of embodiments of an ultrasonic apparatus and an ultrasonic diagnostic method according to the present invention.

Figure 1:
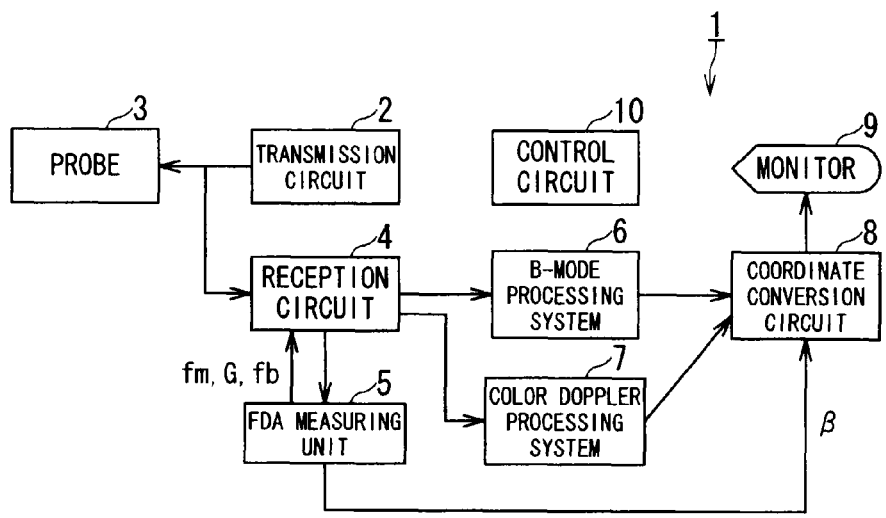
FIG. 1 is a configuration diagram illustrating a first embodiment of the ultrasonic apparatus according to the present invention.

FIG. 1 is a configuration diagram illustrating the first embodiment of the ultrasonic apparatus according to the present invention.

An ultrasonic apparatus 1 has a transmission circuit 2, a probe 3, a reception circuit 4, a frequency dependent attenuation (FDA) measuring unit 5, a B-mode processing system 6, a color Doppler processing system 7, a coordinate conversion circuit 8, a monitor 9, and a control circuit 10.

The transmission circuit 2 has a function of generating a transmitted pulse having a predetermined waveform and a predetermined delay time, and controlling the probe 3 by applying with the generated transmitted pulse so as that the probe 3 transmits an ultrasonic pulse in accordance with the transmitted pulse. Particularly, the transmission circuit 2 is configured to apply the probe 3 with a transmitted pulse having a frequency which is increased over time and a transmitted pulse having a frequency which is reduced over time so as to obtain two types of ultrasonic echoes from the same scan line.

Figure 2:
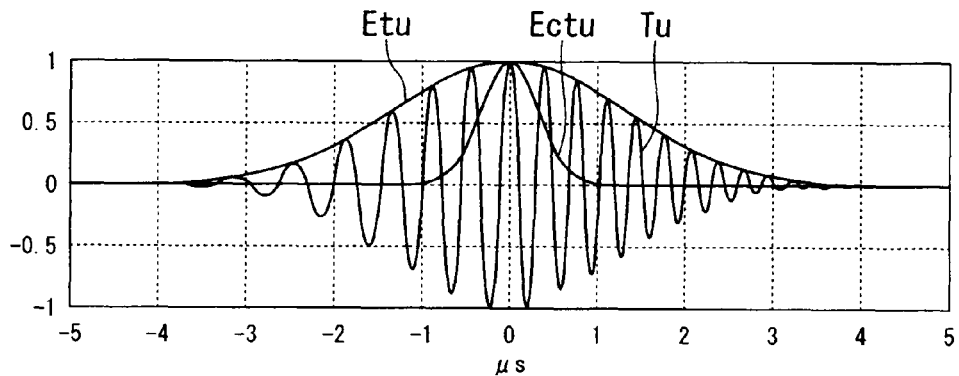
FIG. 2 is a diagram illustrating a transmitted pulse having an up-chirp waveform and applied to a probe by a transmission circuit illustrated in FIG. 1.
Figure 3:
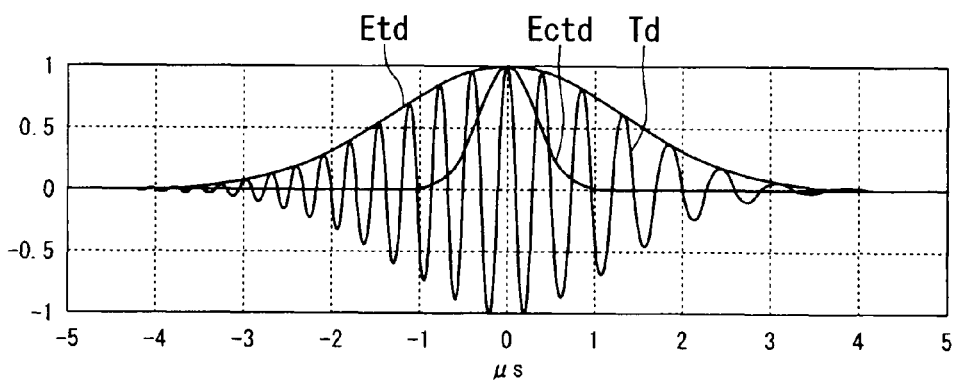
FIG. 3 is a diagram illustrating a transmitted pulse having a down-chirp waveform and applied to the probe by the transmission circuit illustrated in FIG. 1.

FIG. 2 is a diagram illustrating a transmitted pulse having an up-chirp waveform and applied to the probe 3 by the transmission circuit 2 illustrated in FIG. 1. FIG. 3 is a diagram illustrating a transmitted pulse having a down-chirp waveform and applied to the probe 3 by the transmission circuit 2 illustrated in FIG. 1.

In FIGS. 2 and 3, a horizontal axis represents a time [μs], and a vertical axis represents a signal intensity normalized to "1". As an example of the transmitted pulse having a frequency which is increased over time, there is an up-chirp transmitted signal "Tu" which has an envelope curve "Etu" forming the Gaussian waveform, as illustrated in FIG. 2. Further, as an example of the transmitted pulse having a frequency which is reduced over time, there is a down-chirp transmitted signal "Td" which has an envelope curve "Etd" forming the Gaussian waveform, as illustrated in FIG. 3. If the time axis of one of the up-chirp transmitted signal "Tu" illustrated in FIG. 2 and the down-chirp transmitted signal "Td" illustrated in FIG. 3 is reversed, the waveforms of the two signals match each other. That is, the up-chirp transmitted signal "Tu" and the down-chirp transmitted signal "Td" are assumed to be equal to each other in amplitude and frequency, with the reversal of the time axis excluded from consideration. In FIGS. 2 and 3, "Ectu" and "Ectd" indicate envelope curves of signals obtained by pulse compression on the up-chirp transmitted signal "Tu" and the down-chirp transmitted signal "Td", respectively.

The probe 3 includes a plurality of ultrasonic transducers. Each of the ultrasonic transducers has a function of converting the transmitted pulse applied by the transmission circuit 2 into an ultrasonic pulse and transmitting the ultrasonic pulse into an object (not illustrated), and receiving an ultrasonic echo generated along with the transmission of the ultrasonic pulse and outputting the ultrasonic echo to the reception circuit 4 as a received signal.

The reception circuit 4 has a function of generating an IQ (base band) signal by performing amplification, phasing addition, and quadrature phase detection on the received signal obtained from each of the ultrasonic transducers of the probe 3, and supplying the generated IQ signal to the FDA measuring unit 5. The reception circuit 4 further has a function of obtaining correction information from the FDA measuring unit 5 and correcting, with the use of the correction information, the IQ signal or an intermediate signal for generating the IQ signal from the received signal, and a function of supplying the corrected IQ signal to the B-mode processing system 6 and the color Doppler processing system 7.

The correction information of the received signal includes such information as a gain G for correcting the amplitude of the received signal, a mixing frequency fm used in the quadrature phase detection of the received signal, and a center frequency "fb" of a bandpass filter (BPF) 24. The correction information of the received signal need not include all of the gain G for correcting the amplitude of the received signal, the mixing frequency fm used in the quadrature phase detection of the received signal, and the center frequency fb of the bandpass filter 24, and may include at least one thereof.

The FDA measuring unit 5 has a function of calculating, on the basis of the IQ signal obtained from the reception circuit 4, a frequency dependent-attenuation coefficient $\beta$ indicating the amount of the FDA, and a function of supplying the calculated frequency dependent-attenuation coefficient $\beta$ to the coordinate conversion circuit 8. The FDA measuring unit 5 further has a function of generating, on the basis of the frequency dependent-attenuation coefficient $\beta$, the correction information of the received signal for reducing the influence of the FDA, and a function of supplying the generated correction information to the reception circuit 4.

Figure 4:
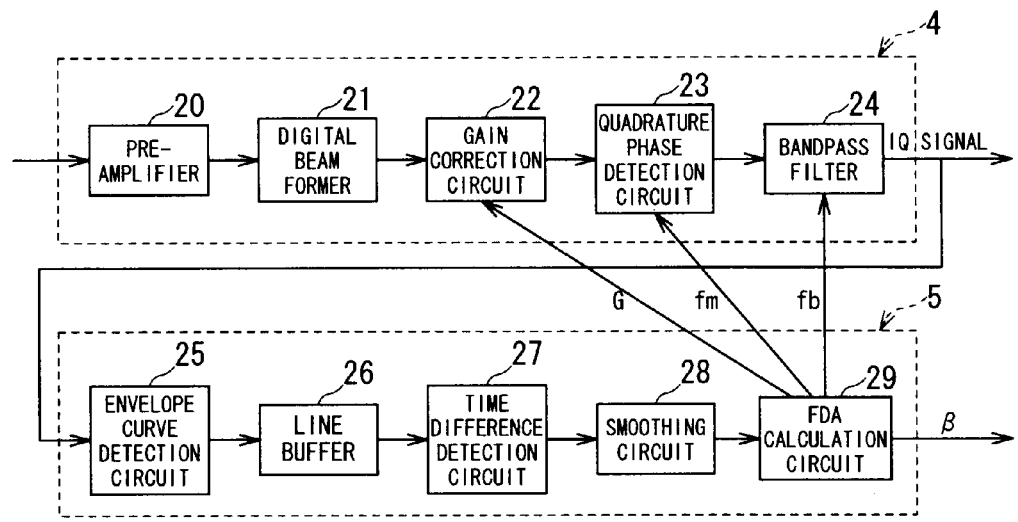
FIG. 4 is a block diagram illustrating a detailed configuration of a reception circuit and an FDA measuring unit illustrated in FIG. 1.

FIG. 4 is a block diagram illustrating a detailed configuration of the reception circuit 4 and the FDA measuring unit 5 illustrated in FIG. 1.

As illustrated in FIG. 4, the reception circuit 4 includes a pre-amplifier 20, a digital beam former 21, a gain correction circuit 22, a quadrature phase detection circuit 23, and the bandpass filter 24. Meanwhile, the FDA measuring unit 5 includes an envelope curve detection circuit 25, a line buffer 26, a time difference detection circuit 27, a smoothing circuit 28, and an FDA calculation circuit 29.

The pre-amplifier 20 of the reception circuit 4 has a function of amplifying the respective received signals obtained from the respective ultrasonic transducers of the probe 3, and outputting the amplified received signals to the digital beam former 21. The digital beam former 21 has a function of performing phasing addition on the plurality of received signals obtained from the pre-amplifier 20 to form a received beam and generate a single received signal.

Herein, the received signal output from the digital beam former 21 has a waveform in accordance with the waveform of the transmitted pulse applied to the probe 3 by the transmission circuit 2.

Figure 5:
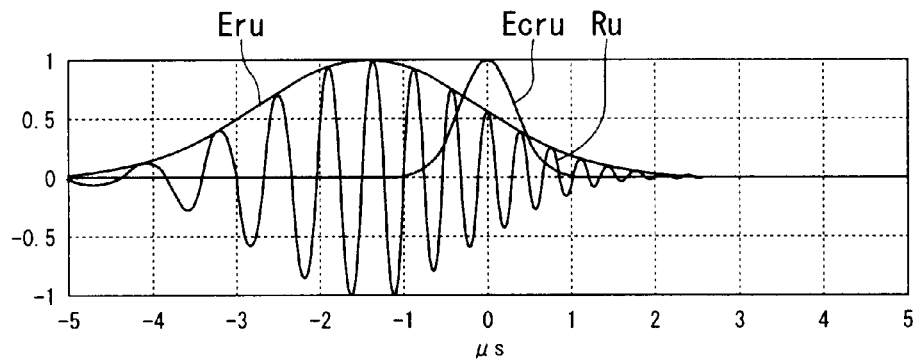
FIG. 5 is a diagram illustrating a waveform of an up-chirp received signal "Ru" affected by an FDA and corresponding to an up-chirp transmitted signal "Tu" illustrated in FIG. 2.
Figure 6:
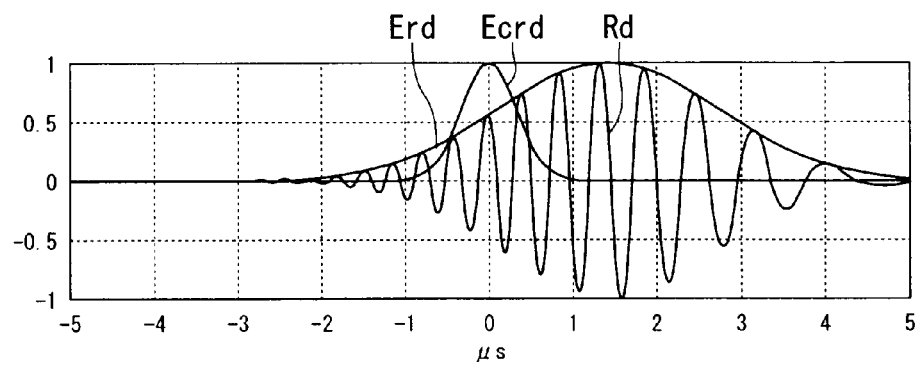
FIG. 6 is a diagram illustrating a waveform of a down-chirp received signal "Rd" affected by the FDA and corresponding to a down-chirp transmitted signal "Td" illustrated in FIG. 3.

FIG. 5 is a diagram illustrating the waveform of an up-chirp received signal Ru affected by the FDA and corresponding to the up-chirp transmitted signal Tu illustrated in FIG. 2. FIG. 6 is a diagram illustrating the waveform of a down-chirp received signal Rd affected by the FDA and corresponding to the down-chirp transmitted signal Td illustrated in FIG. 3.

In FIGS. 5 and 6, the horizontal axis represents the time [μs], and the vertical axis represents the signal intensity normalized to "1". Thus, the amplitude level of the up-chirp transmitted signal "Tu" illustrated in FIG. 2 is practically different from the amplitude level of the up-chirp received signal "Ru" illustrated in FIG. 5. Similarly, the amplitude level of the down-chirp transmitted signal "Td" illustrated in FIG. 3 is different from the amplitude level of the down-chirp received signal "Rd" illustrated in FIG. 6.

Further, in FIGS. 5 and 6, "Ecru" and "Ecrd" indicate envelope curves of signals obtained by pulse compression on the up-chirp received signal "Ru" and the down-chirp received signal "Rd", respectively.

Comparison between FIGS. 5 and 2 reveals that the envelope curve "Eru" of the up-chirp received signal "Ru" shifts to a temporarily earlier direction in comparison with the envelope curve "Etu" of the up-chirp transmitted signal "Tu". In contrast, comparison between FIGS. 6 and 3 reveals that the envelope curve "Erd" of the down-chirp received signal "Rd" shifts to a temporarily delayed direction in comparison with the envelope curve "Etd" of the down-chirp transmitted signal "Td". The temporal shift of the envelope curve "Eru" of the up-chirp received signal "Ru" and the envelope curve "Erd" of the down-chirp received signal "Rd" is attributed to the FDA. As described above, the amount of the FDA is indicated by the frequency dependent-attenuation coefficient $\beta$.

Figure 7:
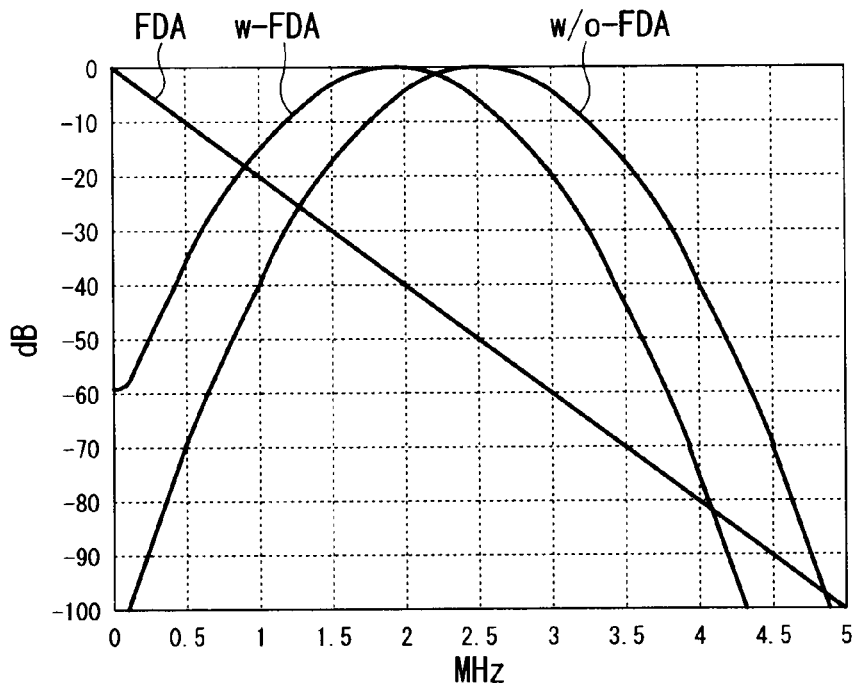
FIG. 7 is a diagram illustrating a frequency dependent-attenuation coefficient β, and respective frequency amplitude characteristics of transmitted signals prior to the FDA and received signals affected by the FDA.

FIG. 7 is a diagram illustrating the frequency dependent-attenuation coefficient $\beta$, and the respective frequency amplitude characteristics of the transmitted signals prior to the FDA and the received signals affected by the FDA.

In FIG. 7, the horizontal axis represents the frequency [MHz], and the vertical axis represents the amplitude [dB] with the maximum value thereof normalized to "1". As illustrated in FIG. 7, FDA represents the frequency dependent-attenuation coefficient $\beta$. Further, w/o-FDA represents the frequency amplitude characteristic common to the up-chirp transmitted signal "Tu" and the down-chirp transmitted signal "Td" prior to the FDA. Meanwhile, w-FDA represents the frequency amplitude characteristic common to the up-chirp received signal "Ru" and the down-chirp received signal "Rd" affected by the FDA.

As illustrated in FIG. 7, in accordance with the value of the frequency dependent-attenuation coefficient $\beta$, the frequency amplitude characteristic w-FDA of the received signals shifts from the frequency amplitude characteristic w/o-FDA of the transmitted signals in the frequency direction. That is, the FDA shifts the center frequency of the received signals from the center frequency of an ideal received signal assumed not affected by the FDA.

Further, the FDA makes the amplitude of the received signals smaller than the amplitude of the ideal received signal assumed not affected by the FDA. In FIG. 7, therefore, the amplitude of the received signals is practically smaller than the amplitude of the transmitted signals.

The gain correction circuit 22 has a function of, when supplied with the gain G from the FDA measuring unit 5, supplying the gain G to the received signal obtained from the digital beam former 21 to correct the amplitude of the received signal attenuated by the FDA. If the gain correction circuit 22 is not supplied with the gain G from the FDA measuring unit 5, the gain correction circuit 22 does not perform the gain correction of the received signal. Further, the gain correction circuit 22 is configured to supply the received signal output therefrom to the quadrature phase detection circuit 23 regardless of whether or not the gain correction has been performed on the received signal.

Figure 8:
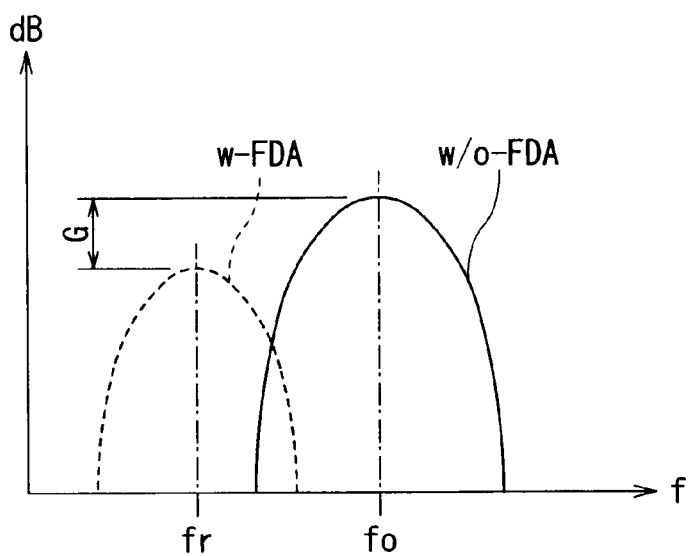
FIG. 8 is a diagram for explaining a method of gain correction by a gain correction circuit illustrated in FIG. 4.

FIG. 8 is a diagram for explaining a method of gain correction by the gain correction circuit 22 illustrated in FIG. 4.

In FIG. 8, the horizontal axis represents the frequency [MHz], and the vertical axis represents the amplitude [dB] of the received signal. Further, in FIG. 8, w-FDA represents the received signal attenuated by the FDA, and w/o-FDA represents the ideal received signal assumed not affected by the FDA.

As illustrated in FIG. 8, the FDA makes the amplitude of the received signal w-FDA having a center frequency fr smaller than the amplitude of the ideal received signal w/o-FDA assumed not affected by the FDA. Therefore, if the amplitude of the received signal w-FDA is corrected with the gain G corresponding to the amount of attenuation of the amplitude of the received signal w-FDA, the amplitude of the received signal w-FDA can be restored to the amplitude of the ideal received signal w/o-FDA assumed not affected by the FDA.

The quadrature phase detection circuit 23 has a function of generating the IQ signal by performing the quadrature phase detection on the received signal obtained from the gain correction circuit 22, and supplying the generated IQ signal to the bandpass filter 24. The quadrature phase detection circuit 23 is configured to perform the quadrature phase detection on the received signal with the mixing frequency fm obtained from the FDA measuring unit 5, which corresponds to the center frequency fr of the received signal affected by the FDA, if the quadrature phase detection circuit 23 has obtained the mixing frequency fm from the FDA measuring unit 5. Through the quadrature phase detection with the mixing frequency fm corresponding to the center frequency fr of the received signal affected by the FDA, the S/N of the IQ signal can be improved.

The bandpass filter 24 is a filter for eliminating a component unnecessary for the generation of ultrasonic diagnostic information from the IQ signal obtained from the quadrature phase detection circuit 23. If the bandpass filter 24 obtains from the FDA measuring unit 5 the center frequency fr of the IQ signal affected by the FDA, the center frequency fb of the filtering is corrected to the center frequency fr of the IQ signal affected by the FDA.

Figure 9:
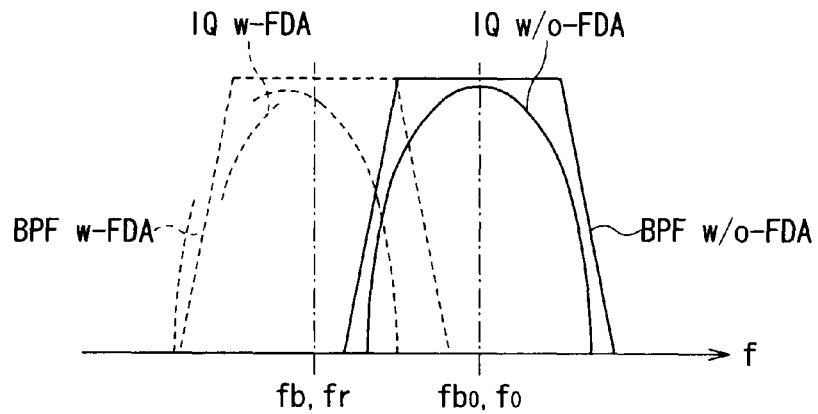
FIG. 9 is a diagram for explaining a method of filtering by a bandpass filter illustrated in FIG. 4.

FIG. 9 is a diagram for explaining a method of filtering by the bandpass filter 24 illustrated in FIG. 4.

In FIG. 9, the horizontal axis represents the frequency [MHz]. Further, IQ w/o-FDA represents an ideal IQ signal assumed not affected by the FDA, and IQ w-FDA represents the IQ signal affected by the FDA.

If the quadrature phase detection circuit 23 performs the quadrature phase detection with the mixing frequency fm corresponding to the center frequency fr of the received signal affected by the FDA, the center frequency fr of the IQ signal affected by the FDA is theoretically equal to a center frequency $fb_0$ of a bandpass filter 24 BPF w/o-FDA which has been set without the consideration of the FDA.

However, if the quadrature phase detection circuit 23 does not perform the quadrature phase detection with the mixing frequency fm corresponding to the center frequency fr of the received signal affected by the FDA, the center frequency $fb_0$ of the bandpass filter 24 BPF w/o-FDA which has been set without the consideration of the FDA is set to a center frequency $f_0$ of the ideal IQ signal IQ w/o-FDA assumed not affected by the FDA, as illustrated in FIG. 9. That is, the center frequency fr of the IQ signal affected by the FDA is different from the center frequency $fb_0$ of the bandpass filter 24 BPF w/o-FDA which has been set without the consideration of the FDA. Thus, the filtering of the IQ signal is performed by a bandpass filter 24 BPF w-FDA, the center frequency fb of which has been corrected to match the center frequency fr of the IQ signal affected by the FDA.

As described above, the correction of the mixing frequency fm for the quadrature phase detection and the correction of the center frequency fb of the bandpass filter 24 can be alternatively selected. In consideration of the correction error, however, both of the correction of the mixing frequency fm and the correction of the center frequency fb of the bandpass filter 24 may be used to reduce the influence of the FDA on the IQ signal ultimately obtained as the output from the bandpass filter 24.

The bandpass filter 24 is configured to output the IQ signal to the B-mode processing system 6, if the IQ signal is for a B-mode image and reflects the correction information obtained from the FDA measuring unit 5, and to output the IQ signal to the color Doppler processing system 7, if the IQ signal is for a color Doppler image and reflects the correction information obtained from the FDA measuring unit 5. Further, the bandpass filter 24 is configured to output the IQ signal to the FDA measuring unit 5, if the IQ signal does not reflect the correction information obtained from the FDA measuring unit 5.

On the other hand, the envelope curve detection circuit 25 of the FDA measuring unit 5 has a function of performing envelope curve detection on the IQ signal obtained from the reception circuit 4, and a function of writing the envelope curve of the obtained IQ signal to the line buffer 26.

Therefore, the envelope curve "Eru" of the up-chirp received signal "Ru" and the envelope curve "Erd" of the down-chirp received signal "Rd" are temporarily stored as a pair in the line buffer 26.

The time difference detection circuit 27 has a function of reading from the line buffer 26 the envelope curve "Eru" of the up-chirp received signal "Ru" and the envelope curve "Erd" of the down-chirp received signal "Rd" and calculating a time difference 2τ between the envelope curve "Eru" of the up-chirp received signal "Ru" and the envelope curve "Erd" of the down-chirp received signal "Rd" (i.e., the amount of positional deviation between the up-chirp received signal "Ru" and the down-chirp received signal "Rd") at sufficiently short time intervals with respect to the accuracy, and a function of outputting the obtained time difference 2τ to the smoothing circuit 28.

The method of calculating the time difference 2τ between the envelope curve "Eru" of the up-chirp received signal "Ru" and the envelope curve "Erd" of the down-chirp received signal "Rd" includes, for example, a method using a mutual correlation function or a SAD (Sum of Absolute Difference) of the envelope curve "Eru" of the up-chirp received signal "Ru" and the envelope curve "Erd" of the down-chirp received signal "Rd". If the mutual correlation function is used, the time difference 2τ is changed as a parameter, and the value of the parameter maximizing the mutual correlation function can be determined as the time difference 2τ. Meanwhile, if the SAD is used, the time difference 2τ is changed as a parameter, and the value of the parameter minimizing the sum of the absolute values of the differences between the envelope curve "Eru" of the up-chirp received signal "Ru" and the envelope curve "Erd" of the down-chirp received signal "Rd" at respective time points can be determined as the time difference 2τ.

The smoothing circuit 28 has a function of smoothing the time difference 2τ between the envelope curve "Eru" of the up-chirp received signal "Ru" and the envelope curve "Erd" of the down-chirp received signal "Rd" obtained from the time difference detection circuit 27, and a function of outputting the smoothed time difference 2τ to the FDA calculation circuit 29. As the method of smoothing, polynomial fitting according to the method of least squares is desirable, for example. However, filtering using a normal LPF (Low Pass Filter) may be used.

The FDA calculation circuit 29 has a function of calculating, on the basis of the smoothed time difference 2τ obtained from the smoothing circuit 28, the correction information of the received signal to be output to the reception circuit 4 and the frequency dependent-attenuation coefficient β, and a function of outputting the calculated correction information of the received signal to the corresponding constituent components of the reception circuit 4 and outputting the frequency dependent-attenuation coefficient β to the coordinate conversion circuit 8. The calculation of the correction information of the received signal and the frequency dependent-attenuation coefficient β uses a parameter ρ of a chirp waveform, the center frequency $f_0$ of the transmitted signal (the received signal assumed not affected by the FDA), and a band parameter "Tg".

Description will now be made of a method of calculating the correction information of the received signal and the frequency dependent-attenuation coefficient β.

The up-chirp received signal "Ru" and the down-chirp received signal "Rd" as illustrated in FIGS. 5 and 6 are obtained from the transmission of the up-chirp transmitted signal "Tu" and the down-chirp transmitted signal "Td" as illustrated in FIGS. 2 and 3, which are equal to each other except for the reversal of the time axis. Thus, if the phase characteristic of the ultrasound apparatus 1 is linear in an ultrasonic transmission and reception band, the up-chirp received signal "Ru" and the down-chirp received signal "Rd" are supposed to match each other in the shape of the envelope curves thereof "Eru" and "Erd", with the time difference 2τ excluded from consideration. Therefore, if the time difference 2τ is changed as a parameter, and if the amount of change is measured when the envelope curves "Eru" and "Erd" match each other, the frequency dependent-attenuation coefficient β can be obtained.

An IQ signal $iq_c(t)$ not affected by the FDA and having an up-chirp waveform forming the Gaussian envelope curve can be expressed as in a following equation (3) using the parameter ρ of the chirp waveform and the band parameter Tg.

$$iq_c(t) = e^{-\pi(1-j\rho)\left(\frac{t}{T_g\sqrt{1+\rho^2}}\right)^2} \tag{3}$$

Fourier transformation $IQ_c(f)$ of the IQ signal $iq_c(t)$ is expressed as in a following equation (4) having separate terms for the amplitude and the phase.

$$IQ_c(f) = T_g A_0 e^{-\pi(T_g f)^2} e^{j\{\theta_0 - \pi\rho(T_g f)^2\}} \tag{4}$$

In the equation, $A_0$ and $\theta_0$ are expressed as follows.

$$A_0 = \sqrt{a^2 + b^2} = \sqrt{2a^2 - 1} = \sqrt[4]{1+\rho^2}$$

$$\theta_0 = \tan^{-1}\frac{b}{a} = \tan^{-1}\frac{\rho}{2a^2} = \tan^{-1}\frac{\rho}{1+\sqrt{1+\rho^2}}$$

If the equation is added with a term $\exp\{-\alpha(f+f_0)\}$ which represents the effect of the FDA with the center frequency $f_0$ of the transmitted signal, a following equation (5) representing Fourier transformation $IQ_\alpha(f)$ of an IQ signal $iq_\alpha(t)$ affected by the FDA is obtained.

$$\begin{aligned}IQ_\alpha(f) &= T_g A_0 e^{-\pi(T_g f)^2} e^{j\{\theta_0 - \pi\rho(T_g f)^2\}} e^{-\alpha(f+f_0)} \\ &= T_g A_0 e^{-\pi T_g^2\left\{\left(f+\frac{\alpha}{2\pi T_g^2}\right)^2 - \frac{\alpha^2}{4\pi^2 T_g^4} + \frac{\alpha f_0}{\pi T_g^2}\right\}} e^{j\theta_0} \\ &\quad \cdot e^{-j\pi\rho T_g^2\left\{\left(f+\frac{\alpha}{2\pi T_g^2}\right)^2 - \frac{\alpha^2}{4\pi^2 T_g^4} - \frac{\alpha f_0}{\pi T_g^2}\right\}} \\ &= T_g A_0 B_\alpha C_\alpha e^{j\theta_0} e^{-\pi\{T_g(f+f_\alpha)\}^2} e^{-j\pi\rho\{T_g(f+f_\alpha)\}^2} e^{j2\pi\tau f}\end{aligned} \tag{5}$$

In the equation, $f_\alpha$, $B_\alpha$, $C_\alpha$, and τ are expressed as follows.

$$f_\alpha = \frac{\alpha}{2\pi T_g^2}$$

$$B_\alpha = e^{-\alpha f_0 + \frac{\alpha}{4\pi}}$$

$$C_\alpha = e^{j\frac{\rho\alpha^2}{4\pi T_g^2}}$$

$$\tau = \frac{\rho\alpha}{2\pi}$$

If an inverse Fourier transformation is performed on the equation (5), a following equation (6) representing the IQ signal $iq_\alpha(t)$ affected by the FDA is obtained.

$$iq_\alpha(t) = B_\alpha C_\alpha e^{j\theta_0} e^{-\pi(1-j\rho)\left(\frac{t+\tau}{T_g\sqrt{1+\rho^2}}\right)^2} e^{-j2\pi f_\alpha(t+\tau)} \tag{6}$$

The equation (6) indicates that the IQ signal $iq_\alpha(t)$ affected by the FDA is different in amplitude and initial phase from the pre-FDA IQ signal $iq_c(t)$ having the up-chirp waveform, and that the IQ signal $iq_\alpha(t)$ has a frequency generally lower than the frequency of the IQ signal $iq_c(t)$ by $f_\alpha$ and an envelope curve earlier from the envelope curve of the IQ signal $iq_c(t)$ by a time τ.

It is understood from the definitional equation of the equation (5) that the mixing frequency fm used in the quadrature phase detection of an RF (radio frequency) received signal can be set to the frequency reduced by the FDA by the frequency decrement $f_\alpha$ from the center frequency $f_0$ of the transmitted signal corresponding to the received signal not affected by the FDA. Therefore, the mixing frequency fm can be calculated as in a following equation (7-1). On the other hand, the gain G for the gain correction of the amplitude of the received signal affected by the FDA is equal to the ratio between the amplitudes of the post-FDA IQ signal $iq_\alpha(t)$ and the pre-FDA IQ signal $iq_c(t)$ deviated from each other by the time τ. Thus, the gain G can be calculated as in a following equation (7-2).

$$f_m = f_0 - f_\alpha = f_0 - \frac{\rho}{(2\pi T_g)^2 r} \quad (7\text{-}1)$$

$$G = \left|\frac{iq_c(t)}{iq_\alpha(t-\tau)}\right| = \frac{1}{B_\alpha} = e^{\alpha f_0 - \frac{\alpha^2}{4\pi T_g^2}} \quad (7\text{-}2)$$

The center frequency fb of the bandpass filter 24 can also be calculated from a similar equation to the equation for calculating the mixing frequency fm used in the quadrature phase detection of the received signal.

On the other hand, the IQ signal $iq_c(t)$ not affected by the FDA and having a down-chirp waveform forming the Gaussian envelope curve can be expressed as in a following equation (8) using the parameter $\rho$ of the chirp waveform and the band parameter Tg.

$$iq_c(t) = e^{-\pi(1+j\rho)\left(\frac{t}{T_g\sqrt{1+\rho^2}}\right)^2} \quad (8)$$

Similarly to the IQ signal $iq_c(t)$ having the up-chirp waveform, the IQ signal $iq_c(t)$ having the down-chirp waveform has an envelope curve delayed by the time $\tau$. When the up-chirp received signal "Ru" is compared with the down-chirp received signal "Rd", therefore, a time difference of $2\tau$ arises. Further, the envelope curve "Eru" of the up-chirp received signal "Ru" and the envelope curve "Erd" of the down-chirp received signal "Rd" are not changed by the FDA.

Therefore, the frequency dependent-attenuation coefficient $\beta$ [dB/MHz/cm] can be calculated from a following equation (9).

$$e^{-\alpha f} = 10^{\frac{\beta*(f*10^{-6})*(2z)}{20}} \quad (9)$$

$$\alpha = \beta z * 10^{-7} \log 10$$

$$\therefore \beta = \frac{10^7}{\log 10}\frac{d\alpha}{dz} = \frac{10^7}{\log 10}\frac{2\pi}{\rho}\frac{d\tau}{dz} = \frac{10^7}{\log 10}\frac{2\pi}{\rho C}\frac{d\tau}{dt}$$

(C: a speed of sonic [cm/s])

In the equation, z represents the depth [cm].

As described above, in the FDA calculation circuit 29, the mixing frequency fm used in the quadrature phase detection of the received signal or the center frequency fb of the bandpass filter 24 are calculated by the equation (7-1), respectively. The gain G used in the gain correction of the received signal is calculated by equation (7-2). Further, the frequency dependent-attenuation coefficient $\beta$ is calculated by the equation (9). A derivative operation of d$\tau$/dt in the equation (9) can be performed by a difference operation.

Further, the FDA calculation circuit 29 is configured to output the gain G used in the gain correction to the gain correction circuit 22, the mixing frequency fm used in the quadrature phase detection of the received signal to the quadrature phase detection circuit 23, the center frequency fb to the bandpass filter 24, and the frequency dependent-attenuation coefficient $\beta$ to the coordinate conversion circuit 8, respectively.

Further, the B-mode processing system 6 has a function of obtaining from the reception circuit 4 the IQ signal for the B-mode image corrected by the correction information obtained from the FDA measuring unit 5, and generating from the IQ signal B-mode image data for displaying a tomographic image of the object, and a function of outputting the generated B-mode image data to the coordinate conversion circuit 8.

The color Doppler processing system 7 has a function of obtaining from the reception circuit 4 the IQ signal for the color Doppler processing corrected by the correction information obtained from the FDA measuring unit 5, detecting a Doppler signal of a blood flow from the IQ signal, and generating color Doppler data for displaying blood flow information, such as the speed of the blood flow, and a function of outputting the generated color Doppler data to the coordinate conversion circuit 8.

The coordinate conversion circuit 8 has a function of performing coordinate conversion processing on the B-mode image data obtained from the B-mode processing system 6 and the color Doppler data obtained from the color Doppler processing system 7, and outputting resultant data to the monitor 9. Thereby, the monitor 9 displays thereon the B-mode image and the color Doppler image in superimposition. The coordinate conversion circuit 8 further has a function of combining, when necessary, the frequency dependent-attenuation coefficient $\beta$ obtained from the FDA measuring unit 5 with the B-mode image data and the color Doppler data. Thus, the coordinate conversion circuit 8 is configured to enable the frequency dependent-attenuation coefficient $\beta$ as well as the B-mode image and the color Doppler image to be displayed on the monitor 9.

The control circuit 10 constitutes a circuit for performing overall control of the transmission circuit 2, the reception circuit 4, the FDA measuring unit 5, the B-mode processing system 6, the color Doppler processing system 7, and the coordinate conversion circuit 8.

Among the above-described constituent components of the ultrasonic apparatus 1, the constituent components for performing information processing can be configured by circuits or a computer which has read a program. Thus, the constituent components configured by the circuits may be substituted by the computer which has read a program. For example, if a control program for the ultrasonic apparatus 1 is read by a computer, the computer can be used as a constituent component for performing the above-described information processing.

Operations and actions of the ultrasonic apparatus 1 will now be described.

Firstly, under the control of the control circuit 10, data is collected to calculate the frequency dependent-attenuation coefficient $\beta$ and the correction information of the received signal in the FDA measuring unit 5. That is, the transmission circuit 2 generates the up-chirp transmitted signals "Tu" having the Gaussian envelope curve "Etu" as illustrated in FIG. 2, as a plurality of transmitted pulses of the number corresponding to the number of the ultrasonic transducers, and applies each of the generated up-chirp transmitted signals "Tu" to the probe 3.

Then, the respective ultrasonic transducers of the probe 3 transmit ultrasonic pulses into the object, and receive ultrasonic echoes generated along with the transmission of the ultrasonic pulses. The respective ultrasonic echoes thus received are output to the reception circuit 4 as the received signals.

In the reception circuit 4, the pre-amplifier 20 amplifies the respective received signals, and the digital beam former 21 performs the phasing addition on the respective received signals thus amplified. As a result, a received beam is formed, and a single received signal is generated. The received signal generated in the above process is the received signal corresponding to the up-chirp transmitted signal "Tu" illustrated in FIG. 2, and is affected by the FDA. Thus, the received signal is equal to the up-chirp received signal "Ru" having the waveform as illustrated in FIG. 5. The up-chirp received signal "Ru" is supplied to the quadrature phase detection circuit 23 via the gain correction circuit 22. The quadrature phase detection circuit 23 performs the quadrature phase detection on the up-chirp received signal "Ru", and supplies the bandpass filter 24 with the generated IQ signal having the up-chirp waveform. The bandpass filter 24 performs filtering on the IQ signal having the up-chirp waveform to eliminate the unnecessary component therefrom, and outputs the filtered IQ signal having the up-chirp waveform to the envelope curve detection circuit 25 of the FDA measuring unit 5. The envelope curve detection circuit 25 detects the envelope curve "Eru" of the IQ signal having the up-chirp waveform, and writes the envelope curve "Eru" to the line buffer 26 to temporality store the envelope curve "Eru" therein.

Next, the transmission circuit 2 generates the down-chirp transmitted signals "Td" having the Gaussian envelope curve "Etd" as illustrated in FIG. 3, as a plurality of transmitted pulses of the number corresponding to the number of the ultrasonic transducers, and applies each of the generated down-chirp transmitted signals "Td" to the probe 3. As a result, in a similar flow to the flow of the up-chirp received signal "Ru", the down-chirp received signal "Rd" from the same scan line as illustrated in FIG. 6 is obtained in the reception circuit 4 as the output from the digital beam former 21. Then, the envelope curve "Erd" of the down-chirp received signal "Rd" is detected by the envelope curve detection circuit 25 and written to the line buffer 26 to be temporarily stored therein.

Then, the time difference detection circuit 27 reads from the line buffer 26 the envelope curve "Eru" of the up-chirp received signal "Ru" and the envelope curve "Erd" of the down-chirp received signal "Rd", and calculates the minimum value of the SAD or the mutual correlation function. Thereby, the time difference detection circuit 27 calculates the time difference 2τ between the envelope curve "Eru" of the up-chirp received signal "Ru" and the envelope curve "Erd" of the down-chirp received signal "Rd" at the sufficiently short time intervals with respect to the accuracy. The smoothing circuit 28 obtains the time difference 2τ from the time difference detection circuit 27, and performs smoothing processing on the time difference 2τ. Then, the smoothing circuit 28 outputs the smoothed time difference 2τ to the FDA calculation circuit 29.

From the time difference 2τ obtained from the smoothing circuit 28, the FDA calculation circuit 29 calculates the gain G for the gain correction performed to reduce the influence of the FDA on the received signal, one or both of the mixing frequency fm used in the quadrature phase detection of the received signal and the center frequency fb of the bandpass filter 24, and the frequency dependent-attenuation coefficient β, respectively. The gain G, the mixing frequency fm, the center frequency fb, and the frequency dependent-attenuation coefficient β thus calculated are output to the gain correction circuit 22, the quadrature phase detection circuit 23, the bandpass filter 24, and the coordinate conversion circuit 8, respectively.

After the frequency dependent-attenuation coefficient β and the correction information of the received signal are obtained as described above, data is then collected to generate the B-mode image or the color Doppler image. That is, in a similar manner as in the data collection for the calculation of the frequency dependent-attenuation coefficient β and the correction information of the received signal, the up-chirp transmitted signal "Tu" and the down-chirp transmitted signal "Td" as illustrated in FIGS. 2 and 3 are sequentially generated and applied to the probe 3 by the transmission circuit 2. Thereby, the up-chirp received signal "Ru" and the down-chirp received signal "Rd" as illustrated in FIGS. 5 and 6 are sequentially obtained as the outputs from the digital beam former 21.

The up-chirp received signal "Ru" and the down-chirp received signal "Rd" for the B-mode image or the color Doppler image are sequentially sent to the gain correction circuit 22 to be subjected to the gain correction with the gain G calculated by the FDA calculation circuit 29. As a result, the amplitude of the up-chirp received signal "Ru" and the amplitude of the down-chirp received signal "Rd" attenuated by the FDA are sequentially corrected.

Next, the up-chirp received signal "Ru" and the down-chirp received signal "Rd" for the B-mode image or the color Doppler image are respectively subjected to the quadrature phase detection by the quadrature phase detection circuit 23. The respective IQ signals obtained from the quadrature phase detection are filtered by the bandpass filter 24. In the above process, the quadrature phase detection is performed with the mixing frequency fm calculated by the FDA calculation circuit 29, or the filtering is performed by the bandpass filter 24 with the center frequency fb calculated by the FDA calculation circuit 29. As a result, the center frequency fr of each of the up-chirp received signal "Ru" and the down-chirp received signal "Rd" shifted by the FDA is corrected.

Next, if the IQ signals are for the B-mode image, the IQ signals are output from the reception circuit 4 to the B-mode processing system 6. Meanwhile, if the IQ signals are for the color Doppler image, the IQ signals are output from the reception circuit 4 to the color Doppler processing system 7. The B-mode processing system 6 generates from the IQ signals for the B-mode image the B-mode image data for displaying the tomographic image of the object, and outputs the generated B-mode image data to the coordinate conversion circuit 8. On the other hand, the color Doppler processing system 7 detects the Doppler signal from the IQ signals for the color Doppler image, generates the color Doppler data for displaying the blood flow information, such as the speed of a blood flow, and outputs the generated color Doppler data to the coordinate conversion circuit 8.

The coordinate conversion circuit 8 performs the coordinate conversion processing on the distribution information of the frequency dependent-attenuation coefficient β obtained from the FDA measuring unit 5, the B-mode image data obtained from the B-mode processing system 6, and the color Doppler data obtained from the color Doppler processing system 7, and outputs the resultant data to the monitor 9. Thereby, the monitor 9 displays thereon the B-mode image and the color Doppler image in superimposition. The monitor 9 further displays thereon the distribution information of the frequency dependent-attenuation coefficient β at respective scan positions.

That is, the above-described ultrasonic apparatus 1 transmits the transmitted pulse having such a waveform as the up-chirp waveform in which the frequency is increased over time, and the transmitted pulse having such a waveform as the down-chirp waveform in which the frequency is reduced over time, to thereby obtain the ultrasonic frequency dependent-attenuation characteristic from the time difference between the envelope curves of the received signals corresponding to the respective transmitted pulses.

According to the above-described ultrasonic apparatus 1, the FDA can be calculated in a simplified manner by a simple process of measuring the time difference between two types of received signals. Particularly, if the up-chirp signal and the down-chirp signal form the transmitted pulses, the received signals are also formed by the up-chirp signal and the down-chirp signal. Thus, the calculation of the frequency dependent-attenuation is simplified. Further, the transmission of a chirp-signal does not involve pulse compression decoding. Thus, a circuit for performing complicated decoding is unnecessary.

Further, the ultrasonic apparatus 1 can correct, when necessary, the amplitude and the frequency of the received signal with the use of the calculated frequency dependent-attenuation coefficient β. Thus, the influence of the FDA on the received signal can be reduced.

Figure 10:
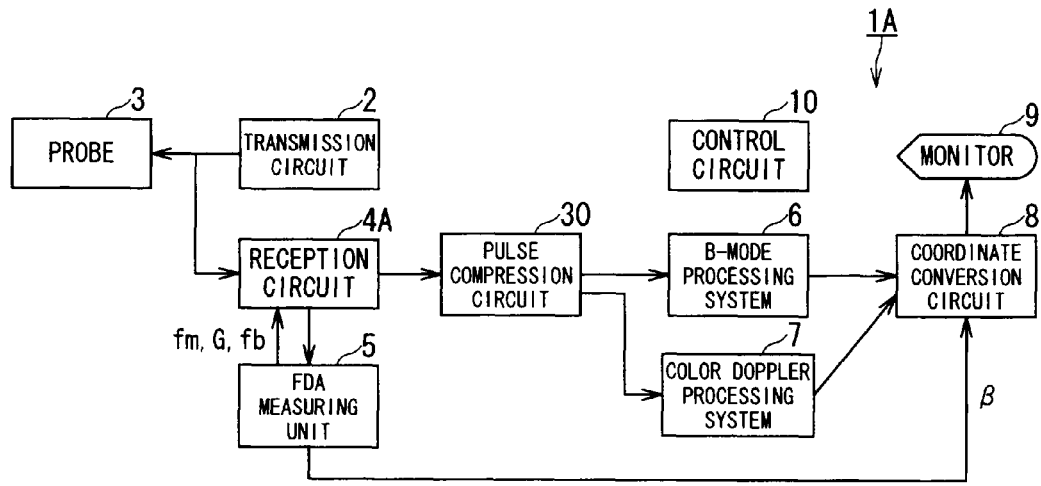
FIG. 10 is a configuration diagram illustrating a second embodiment of the ultrasonic apparatus according to the present invention.

FIG. 10 is a configuration diagram illustrating the second embodiment of the ultrasonic apparatus according to the present invention.

An ultrasonic apparatus 1A illustrated in FIG. 10 is different from the ultrasonic apparatus 1 illustrated in FIG. 1 in a configuration including a pulse compression circuit 30 provided on the output side of a reception circuit 4A, a detailed configuration of the reception circuit 4A, and a signal processing flow. The ultrasonic apparatus 1A is not substantially different from the ultrasonic apparatus 1 illustrated in FIG. 1 in the other configurations and actions. Thus, the same configurations are assigned with the same reference numerals, and description thereof will be omitted.

As illustrated in FIG. 10, the output of the reception circuit 4A of the ultrasonic apparatus 1A is connected to the pulse compression circuit 30. Further, the output of the pulse compression circuit 30 is connected to the B-mode processing system 6 and the color Doppler processing system 7.

Figure 11:
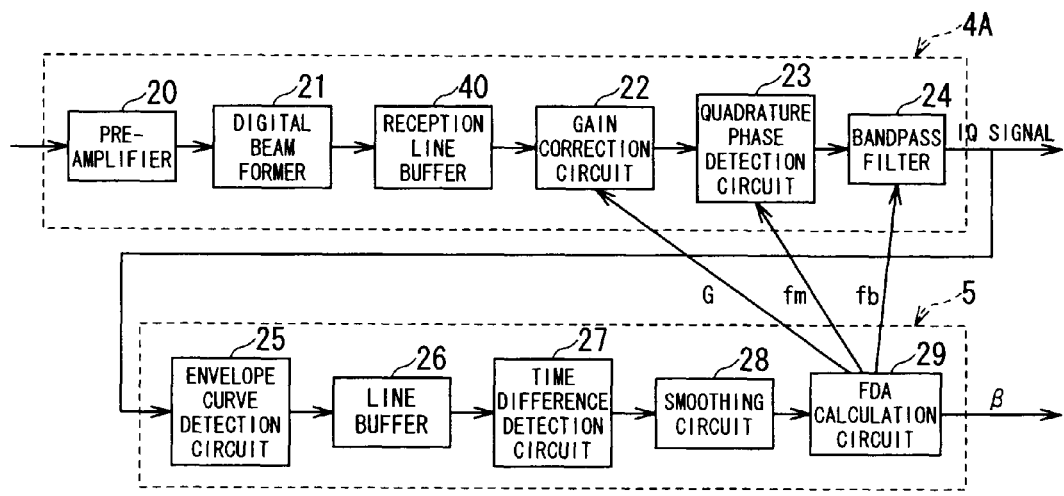
FIG. 11 is a block diagram illustrating a detailed configuration of a reception circuit and the FDA measuring unit illustrated in FIG. 10.

FIG. 11 is a block diagram illustrating a detailed configuration of the reception circuit 4A and the FDA measuring unit 5 illustrated in FIG. 10. In FIG. 11, the same configurations as the configurations of the reception circuit 4 illustrated in FIG. 4 are assigned with the same reference numerals, and description thereof will be omitted.

As illustrated in FIG. 11, a reception line buffer 40 is connected between the digital beam former 21 and the gain correction circuit 22 of the reception circuit 4A. The reception line buffer 40 is configured to temporarily store a plurality of received signals output from the digital beam former 21.

In the thus configured ultrasonic apparatus 1A, the data collection is not performed separately for the generation of the B-mode image or the color Doppler image and the calculation of the frequency dependent-attenuation coefficient β and the correction information of the received signal, but a single received signal is used for both the generation of the image and the calculation of the frequency dependent-attenuation coefficient β and the correction information of the received signal. That is, after the IQ signal is generated from the quadrature phase detection and the filtering performed on the received signal output from the digital beam former 21, the generated IQ signal is output to the FDA measuring unit 5 for the calculation of the frequency dependent-attenuation coefficient β and the correction information of the received signal.

Subsequently, the correction information of the received signal is supplied to the gain correction circuit 22, the quadrature phase detection circuit 23, and the bandpass filter 24, and the same received signal is read from the reception line buffer 40. Then, the same received signal is subjected to the gain correction with the gain G and the quadrature phase detection with the mixing frequency fm or the filtering by the bandpass filter 24 with the center frequency fb.

That is, the received signal obtained from the same site twice passes the gain correction circuit 22, the quadrature phase detection circuit 23, and the bandpass filter 24. From the IQ signal generated in the first passage of the received signal, the frequency dependent-attenuation coefficient β and the correction information of the received signal are calculated. Then, in the second passage of the received signal, another IQ signal is generated in accordance with the optimal gain correction, quadrature phase detection, and filtering reflecting the correction information of the received signal.

The IQ signal generated in the second passage is output from the reception circuit 4A to the pulse compression circuit 30. The pulse compression circuit 30 performs pulse compression on the IQ signal output from the reception circuit 4A. As a result, the pulse-compressed IQ signals as illustrated in FIGS. 5 and 6 are obtained. To maximize the S/N, the pulse compression may be performed by matched filtering on a kernel having a complex conjugate, with the reversal of the time axis of the IQ signal $iq_c(t)$ expressed by the equation (3). Alternatively, to maximize the resolution, the pulse compression may be performed by a method of performing only phase correction.

If the mixing frequency fm used in the quadrature phase detection of the received signal is changed, a time deviation occurs. Therefore, if the mixing is performed on the received signal in the reception circuit 4A with the center frequency $f_0$ of the transmitted signal without the correction of the mixing frequency fm used in the quadrature phase detection of the received signal, the time control of the IQ signal after the pulse compression processing is easily performed. That is, the time deviation due to the FDA does not occur in the pulse-compressed IQ signal, as long as the IQ signal is generated from the mixing with the center frequency $f_0$ of the transmitted signal and the quadrature phase detection performed on the received signal. Thus, if the mixing is performed on the received signal with the center frequency $f_0$ of the transmitted signal, the pulse-compressed IQ signal can be used as a normal signal for generating the B-mode image or the color Doppler image. Therefore, the pulse-compressed IQ signal is output to the B-mode processing system 6 and the color Doppler processing system 7.

To improve the S/N, however, it is desired to perform the mixing in the reception circuit 4A with the mixing frequency fm corresponding to the center frequency fr of the received signal affected by the FDA, and to correct the time deviation occurring in the IQ signal after the pulse compression. Therefore, in the mixing of the received signal with the mixing frequency fm corresponding to the center frequency fr of the received signal affected by the FDA, the time deviation occurring in the IQ signal is corrected in the pulse compression circuit 30. Then, the IQ signal subjected to the pulse compression and the correction of the time deviation is output from the pulse compression circuit 30 to the B-mode processing system 6 and the color Doppler processing system 7.

According to the thus configured ultrasonic apparatus 1A, there is no need to collect data only to calculate the frequency dependent-attenuation coefficient β and the correction information of the received signal. Thus, the number of data collections and the number of data sets can be reduced. Further, the S/N can be improved due to the pulse compression.

Figure 12:
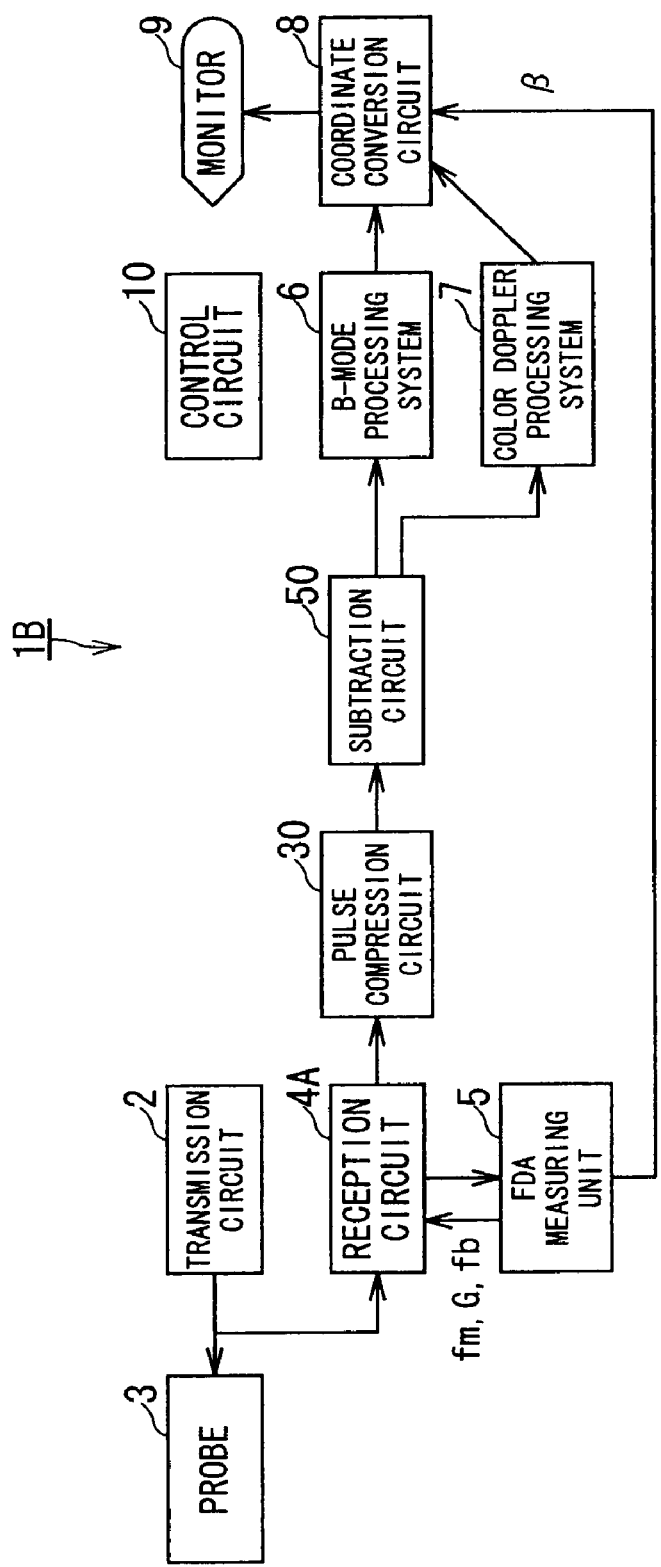
FIG. 12 is a configuration diagram illustrating a third embodiment of the ultrasonic apparatus according to the present invention.

FIG. 12 is a configuration diagram illustrating the third embodiment of the ultrasonic apparatus according to the present invention.

A ultrasonic apparatus 1B illustrated in FIG. 12 is different from the ultrasonic apparatus 1A illustrated in FIG. 10 in a configuration including a subtraction circuit 50 provided on the output side of the pulse compression circuit 30, and signal processing in the data collection according to a contrast echo method using an ultrasonic contrast agent. The ultrasonic apparatus 1B is not substantially different from the ultrasonic apparatus 1A illustrated in FIG. 10 in the other configurations and actions. Thus, the same configurations are assigned with the same reference numerals, and description thereof will be omitted.

In the ultrasonic apparatus 1B, the output of the pulse compression circuit 30 is connected to the subtraction circuit 50. Further, the output of the subtraction circuit 50 is connected to the B-mode processing system 6 and the color Doppler processing system 7. The subtraction circuit 50 performs subtraction processing between the two pulse-compressed IQ signals obtained by the pulse compression circuit 30 and corresponding to the up-chirp received signal "Ru" and the down-chirp received signal "Rd". That is, one of the pulse-compressed IQ signal corresponding to the up-chirp received signal "Ru" and the pulse-compressed IQ signal corresponding to the down-chirp received signal "Rd" is subtracted from the other one of the IQ signals.

In the above process, the result of the pulse compression on the up-chirp received signal "Ru" matches the result of the pulse compression on the down-chirp received signal "Rd" in a linear response. Therefore, a linear echo component obtained from a tissue is cancelled in the pulse-compressed IQ signal obtained from the subtraction.

In the data collection according to the contrast echo method using the ultrasonic contrast agent, the received signal obtained from the bubbles of the ultrasonic contrast agent is subjected to the signal processing. The up-chirp received signal "Ru" and the down-chirp received signal "Rd" obtained from the bubbles of the ultrasonic contrast agent show mutually different responses. Therefore, if one of the pulse-compressed IQ signal corresponding to the up-chirp received signal "Ru" and the pulse-compressed IQ signal corresponding to the down-chirp received signal "Rd" is subtracted from the other one of the IQ signals, a signal from the ultrasonic contrast agent remains. Then, if the signal remaining after the subtraction is visualized, an image from the ultrasonic contrast agent can be obtained.

That is, the subtraction circuit 50 extracts a contrast signal obtained from an ultrasonic echo signal emitted from the ultrasonic contrast agent. Then, the extracted contrast signal is output to the B-mode processing system 6 and the color Doppler processing system 7, and the B-mode image data and the color Doppler data are generated from the contrast signal.

In the above process, the amplitude of the received signal constituting the basis of the contrast signal has been corrected with the gain G in the reception circuit 4A to the amplitude of the received signal assumed not affected by the FDA. Thus, the intensity of the contrast signal, i.e., the intensity of the contrast produced by the ultrasonic contrast agent has a quantitative characteristic irrespective of the differences in the depth and the site from which the signal is obtained. In the B-mode image and the color Doppler image displayed on the monitor 9, therefore, the comparison of the contrast intensity shown as the luminance can be performed irrespective of the differences in the depth and the site.

That is, if the signal from a tissue is suppressed and the echo signal is extracted from the bubbles of the ultrasonic contrast agent through the subtraction between the IQ signals, as in the ultrasonic apparatus 1B, the luminance of a contrasted region can be quantitatively evaluated in the B-mode image and the color Doppler image irrespective of the depth and the site, since the received signal from the ultrasonic contrast agent has been subjected to the amplitude correction in which the amplitude is multiplied by the gain G in accordance with the FDA.

In the above-described ultrasonic apparatuses 1, 1A, and 1B, the up-chirp signal and the down-chirp signal are assumed to be transmitted and received on the same scan line. However, a slight deviation between the scan lines does not cause a rapid change in the FDA. Therefore, the up-chirp signal and the down-chirp signal do not necessary need to be transmitted and received on the same scan line. Particularly, when the smoothing circuit 28 performs two-dimensional smoothing on the value of the time difference 2τ in the distance direction and the azimuth direction, the deviation between the scan lines on which the up-chirp signal and the down-chirp signal are transmitted and received hardly affects the frequency dependent-attenuation coefficient β and the correction information of the received signal. Rather, the frame rate can be improved by the deviation between the scan lines on which the up-chirp signal and the down-chirp signal are transmitted and received.

Further, the probe 3 may be configured by a two-dimensional array probe to three-dimensionally transmit and receive the up-chirp signal and the down-chirp signal. In such a case, the frequency dependent-attenuation coefficient β is obtained as a three-dimensional distribution.

Further, the ultrasonic apparatuses 1, 1A, and 1B are configured such that the received signal for the B-mode image and the received signal constituting the basis of the Doppler signal are corrected to thereby correct the B-mode image data and the blood flow information, such as the speed of a blood flow, obtained from the Doppler signal. Alternatively, the B-mode image data and the blood flow information such as the speed of a blood flow may be directly subjected to the correction using the frequency dependent-attenuation coefficient β or the value for reducing the influence of the FDA.

What is claimed is:

1. An ultrasonic apparatus, comprising:
    a pulse transmission and reception unit configured to transmit a first transmitted pulse in which a frequency increases with time and a second transmitted pulse in which the frequency decreases with time, and to receive a first received pulse corresponding to the first transmitted pulse and a second received pulse corresponding to the second transmitted pulse;
    an envelope curve detection unit configured to detect a first envelope curve based on the first received pulse and a second envelope curve based on the second received pulse, respectively;
    a time difference detection unit configured to detect a first time lag from a transmitted time of the first transmitted pulse to a received time of the first received pulse based on the first envelope curve, to detect a second time lag from a transmitted time of the second transmitted pulse to a received time of the second received pulse based on the second envelope curve, and to detect a time difference between the first time lag and the second time lag; and
    an attenuation characteristic obtaining unit configured to obtain a frequency dependent-attenuation characteristic based on the detected time difference.

2. An ultrasonic apparatus according to claim 1, wherein the pulse transmission and reception unit is configured to transmit an up-chirp signal as the first transmitted pulse, for which an envelope curve is a Gaussian waveform, and to transmit a down-chirp signal as the second transmitted pulse, for which the envelope curve is the Gaussian waveform.

3. An ultrasonic apparatus according to claim 1, further comprising:
    a pulse compression unit configured to compress a pulse of the first received pulse and the second received pulse.

4. An ultrasonic apparatus according to claim 1, wherein the pulse transmission and reception unit is configured to three-dimensionally transmit the first transmitted pulse and the second transmitted pulse, and the attenuation characteristic obtaining unit is configured to obtain the frequency dependent-attenuation characteristic as a three-dimensional distribution.

5. An ultrasonic apparatus according to claim 1, further comprising:
a correction unit configured to correct at least one of a mixing frequency used in the quadrature phase detection of the first received pulse and the second received pulse according to the frequency dependent-attenuation coefficient, a filter characteristic used for performing a filtering of the first received pulse and the second received pulse, and an amplitude of the first received pulse and the second received pulse.

6. An ultrasonic apparatus according to claim 1, further comprising:
a speed correction unit configured to correct a speed obtained based on a Doppler signal by using the frequency dependent-attenuation characteristic.

7. An ultrasonic apparatus according to claim 1, further comprising:
a correction unit configured to correct an amplitude of the first received pulse and the second received pulse by using the frequency dependent-attenuation characteristic;
a pulse compression unit configured to compress a pulse of the first received pulse and the second received pulse; and
a contrast signal extraction unit configured to extract a contrast signal from an ultrasonic contrast agent by reducing one of the first received pulse and the second received pulse from the other of the first received pulse and the second received pulse.

8. An ultrasonic diagnostic method, comprising:
generating a pulse for applying a first transmitted pulse, in which a frequency increases with time and a second transmitted pulse, in which the frequency decreases with time, to a probe;
receiving a first received pulse corresponding to the first transmitted pulse and a second received pulse corresponding to the second transmitted pulse;
detecting a first envelope curve based on the first received pulse and a second envelope curve based on the second received pulse, respectively;
detecting a first time lag from a transmitted time of the first transmitted pulse to a received time of the first received pulse based on the first envelope curve, detecting a second time lag from a transmitted time of the second transmitted pulse to a received time of the second received pulse based on the second envelope curve, and detecting a time difference between the first time lag and the second time lag; and
an attenuation characteristic obtaining step of obtaining a frequency dependent-attenuation characteristic based on the detected time difference.

9. An ultrasonic diagnostic method according to claim 8, wherein the pulse generation step comprises generating an up-chirp signal as the first transmitted pulse, for which the envelope curve is a Gaussian waveform, and a down-chirp signal as the second transmitted pulse, for which the envelope curve is the Gaussian waveform.

10. An ultrasonic diagnostic method according to claim 8, further comprising:
compressing a pulse of the first received pulse and the second received pulse.

11. An ultrasonic diagnostic method according to claim 8, wherein the pulse generation step comprises three-dimensionally generating the first transmitted pulse and the second transmitted pulse, and the attenuation characteristic obtaining step obtains the frequency dependent-attenuation characteristic as a three-dimensional distribution.

12. An ultrasonic diagnostic method according to claim 8, further comprising:
correcting at least one of a mixing frequency used in the quadrature phase detection of the first received pulse and the second received pulse according to the frequency dependent-attenuation coefficient, a filter characteristic used for performing a filtering of the first received pulse and the second received pulse, and an amplitude of the first received pulse and the second received pulse.

13. An ultrasonic diagnostic method according to claim 8, further comprising:
correcting a speed obtained based on a Doppler signal by using the frequency dependent-attenuation characteristic.

14. An ultrasonic diagnostic method according to claim 8, further comprising:
correcting an amplitude of the first received pulse and the second received pulse by using the frequency dependent-attenuation characteristic;
compressing a pulse of the first received pulse and the second received pulse; and
extracting a contrast signal from an ultrasonic contrast agent by reducing one of the first received pulse and the second received pulse from the other of the first received pulse and the second received pulse.

15. The ultrasonic diagnostic apparatus of claim 1, wherein the pulse transmission and reception unit is configured to receive the first and second pulses from a same scan line.

* * * * *